United States Patent [19]

Van Der Puy et al.

[11] Patent Number: 4,540,428
[45] Date of Patent: Sep. 10, 1985

[54] PHOSPHOROTRIAMIDATE UREASE INHIBITORS AND UREASE INHIBITED UREA BASED FERTILIZER COMPOSITIONS

[75] Inventors: Michael Van Der Puy, Cheektowaga; Larry L. Hendrickson, Camillus, both of N.Y.; Jaroslav F. Kolc, Randolph Township, Dover County, N.J.; Milorad M. Rogic, Whippany, N.J.; Michael D. Swerdloff, Parsippany, N.J.

[73] Assignee: Allied Corporation, Morris Township, Morris County, N.J.

[21] Appl. No.: 475,980

[22] Filed: Mar. 16, 1983

[51] Int. Cl.³ .................................................. C05C 9/00
[52] U.S. Cl. ............................................ 71/28; 71/902
[58] Field of Search .................................. 71/11, 27–30, 71/902

[56] References Cited

U.S. PATENT DOCUMENTS

| | | | |
|---|---|---|---|
| 3,388,989 | 6/1968 | Sor | 71/28 |
| 3,523,018 | 8/1970 | Geissler et al. | 71/28 |
| 3,565,599 | 5/1969 | Sor et al. | 71/28 |
| 4,182,881 | 1/1980 | Bayless et al. | 546/22 |
| 4,222,948 | 9/1980 | Alaimo et al. | 260/397.7 R |
| 4,225,526 | 9/1980 | Alaimo et al. | 260/397.7 R |
| 4,242,325 | 12/1980 | Bayless et al. | 424/210 |

FOREIGN PATENT DOCUMENTS

| | | |
|---|---|---|
| 830800 | 3/1960 | United Kingdom . |
| 1494774 | 12/1977 | United Kingdom . |

OTHER PUBLICATIONS

1978, CA, vol. 89, Abst. #89:89455k, Matzel et al.
1979, CA, vol. 90, Abst. #90:21340j, Oertel et al.
1979, CA, vol. 91, Abst. #91:122724p, Matzel et al.
1979, CA, vol. 91, Abst. #91:139619f, Heber et al.
1981, CA, vol. 94, Abst. #94:101951g, Vlek et al.
1981, CA, vol. 94, Abst. #94:139429f, Bayless et al.

Primary Examiner—Ferris H. Lander
Attorney, Agent, or Firm—Richard C. Stewart, II

[57] ABSTRACT

The invention rleates to novel urease inhibited fertilizer compositions containing urea, a urease inhibiting effective amount of phosphorotriamidate compounds, and a method and composition for using such compounds to inhibit the activity of urease.

42 Claims, 1 Drawing Figure

PHOSPHOROTRIAMIDATE UREASE INHIBITORS AND UREASE INHIBITED UREA BASED FERTILIZER COMPOSITIONS

BACKGROUND OF THE INVENTION

1. Field of the Invention

This invention relates to novel phosphorotriamidate urease inhibitors and to urease inhibited urea based fertilizer compositions. More particularly, this invention relates to urease inhibited urea based fertilizer compositions which contain certain phosphorotriamidate compounds as the urease inhibitors, and methods of using such fertilizer compositions to increase plant yield and methods of and compositions for inhibiting the catalytic activity of urease by such phosphorotriamidate compounds.

2. The Prior Art

It is well known in the art to use urea and urea compositions in fertilizers for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonias, when urea is placed under or on the surface of moist soil which contains urease. Urease, a crystallizable enzyme occurring in numerous bacteria and fungi, as for example *Micrococcus urease,* catalyzes the conversion of urea into ammonia and carbon dioxide. Carbonate which subsequently decomposes into ammonium bicarbonate and ammonia. The reactions are as follows:

$$CO(NH_2)_2 + 2H_2O \xrightarrow{Urease} 2NH_3 + H_2CO_3$$

$$2NH_3 + H_2O \longrightarrow NH_4^+ + OH^-$$

A portion of the ammonia thus formed is held by absorbing constituents of the soil and is available to plants as nutrient. However, a large amount of the ammonia may be lost to the air. A further problem resulting from the action of urease is that the accumulation of ammonium in the soil and rise in problems, including damage to germinating seedlings and young plants.

One approach to reduction of problems resulting from the activity of soil urease toward soil applied urea is to find compounds that inhibit urease activity when applied to soils in conjunction with fertilizer urea. This approach has received considerable attention, and several compounds have been used. For example, U.S. Pat. No. 3,388,989 discloses a fertilizer composition consisting of urea, a hydrocarbon binder and a urease inhibitor such as formaldehyde, boron metal salts such as sodium borate and potassium borate, fluorine metal salts and heavy metal ions with atomic weights greater than 50.00. U.S. Pat. No. 3,523,018 describes the use of inorganic or organic heavy metal salts such as copper sulfate, borax, and addition compounds of cupric copper formate and copper acetate as urease inhibitors. U.S. Pat. No. 3,565,599 describes a fertilizer composition which contains urea, certain hydrophobic chemicals and an inorganic boron compound as for example, orthoboric acid, sodium perborate, potassium metaborates, tetraboric acid, ammonium pentaborate and ammonium tetraborate.

Other prior art describes various phosphoro compounds which are useful as urease inhibitors. For example, East German Pat. Nos. 142,714; 212,026; 122,177; 122,621 and 130,936, and Great Britain Pat. No. 1,494,774 describe various phosphorodiamidates as urease inhibitors. U.S. Pat. No. 4,242,325 describes a method of controlling the enzymatic decomposition of urea to ammonia and carbonic acid due to the action of urease which comprises exposing the enzyme to certain phosphorotriamidate compounds. U.S. Pat. No. 4,182,881 describes the use of certain N-[diamino-phosphinyl]arylcarboxyamide compounds as inhibitors of the enzyme urease in the urinary tract. U.S. Pat. No. 4,225,526 describes the use of 8-[(4-aminophenyl)-sulfonyl]amino-2-napthalenyl phosphorodiamidate compounds as inhibitors of the enzyme urease, and U.S. Pat. No. 4,222,948 describes the use of [(4-aminophenyl)sulfonyl]amino]phenyl phosphorodiamidate compounds as inhibitors of the enzyme urease.

Still other prior art describes phosphorotriamidate compounds which are useful for other purposes, for example as flame proofing agents. For example, Great Britain Pat. No. 830,800 describes certain phosphorotriamide compounds which are useful as flame proofing agents.

SUMMARY OF THE INVENTION

In accordance with the present invention, there is provided a unique fertilizer composition comprising urea or a compound which is capable of forming urea when subjected to the use conditions of the composition and a urease inhibiting amount of one or more phosphorotriamidate compounds of the formula:

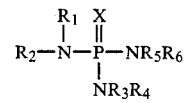

wherein:
X is oxygen or sulfur;
$R_1$ is alkyl substituted with one or more "nucleophilic substituents";
$R_2$ is $R_1$, hydrogen, or substituted or unsubstituted cycloalkenyl, alkenyl, alkynyl, cycloalkyl, aralkyl, alkyl, aryl or alkaryl wherein permissible substituents are one or more trihalomethyl, alkyl, halogen, naphthoxy, phenoxy, arylcarbonyl, phenyl, nitro, cyano, amino, alkylamino, dialkylamino, arylmercapto, alkoxy, mercapto, alkylmercapto, alkylcarbonyl, alkoxycarbonyl, arylcarbonyl, carboxy, arylamino, diarylamino, or carbonamide; and
$R_3$, $R_4$, $R_5$ and $R_6$ are individually hydrogen or alkyl having from 1 to about 4 carbon atoms.

Hereinafter the term "phosphorotriamidate compound" will be used to refer to the compounds of the above-referenced structural formula.

"Nucleophilic substituents" are well known to those of skill in the chemical arts and as used herein are groups which are Lewis bases which can donate electrons. Such groups are described in great detail in March, Jerry, "Advanced Organic Chemistry: Reactions, Mechanisms and Structure", McGraw-Hill Book Company, Inc., 1968, pp. 199 and 200, and Hine, Jack, "Physical Organic Chemistry", McGraw-Hill Book Company, Inc., 1956, pp. 46 and 47, and 86 to 88.

Another aspect of this invention relates to a method of enhancing the yield of plants which comprises applying to the "plant growth medium" an effective amount of the fertilizer composition of this invention within reach of root system of the plant hereinafter referred to as "root zone". The term "plant growth medium" as herein employed refers to various natural and artificial media which support plant growth, including but not limited to soil, potting mixtures of organic and inorganic matter and artificial media such as polyurethane foams.

Yet another aspect of this invention relates to a method of inhibiting the action of urease against urea applied to a plant growth medium which comprises distributing in said plant growth medium "a urease inhibiting effective amount" of one or more of the above-identified phosphorotriamidate compounds prior to, after or in conjunction with the application of urea to said plant growth media. Still another aspect of this invention relates to a composition comprising a "urease inhibiting effective amount" of one or more of such phosphorotriamidate compounds useful for carrying out the aforesaid method. As used herein a "urease inhibiting effective amount" is an amount of one or more of the said phosphorotriamidate compounds which when admixed with urea (or one or more urea precursor compounds capable of forming urea in situ under the use conditions of the compounds), or applied to a "plant growth medium" before, after or in conjunction with application of urea or such compound to the plant growth medium, is capable of inhibiting the catalytic activity of urease that may be in the said plant growth medium to any extent.

It has been discovered by distributing a urease inhibiting effective amount of one or more of the aforesaid phosphorotriamidate compounds in the plant growth medium the urease catalyzed hydrolysis of urea to ammonia is suppressed thereby preventing the rapid loss of urea from the medium. Furthermore, by proper distribution such one or more phosphorotriamidate compounds, this action of inhibiting the urease hydrolysis of urea to ammonia is effective over a prolonged period of time.

BRIEF DESCRIPTION OF THE DRAWING

The drawing is a graph of urea hydrolyzed as a function of time at 35° C. using 10 micrograms of urease inhibitor per gram of soil.

DETAILED DESCRIPTION OF THE INVENTION

Figure 1:
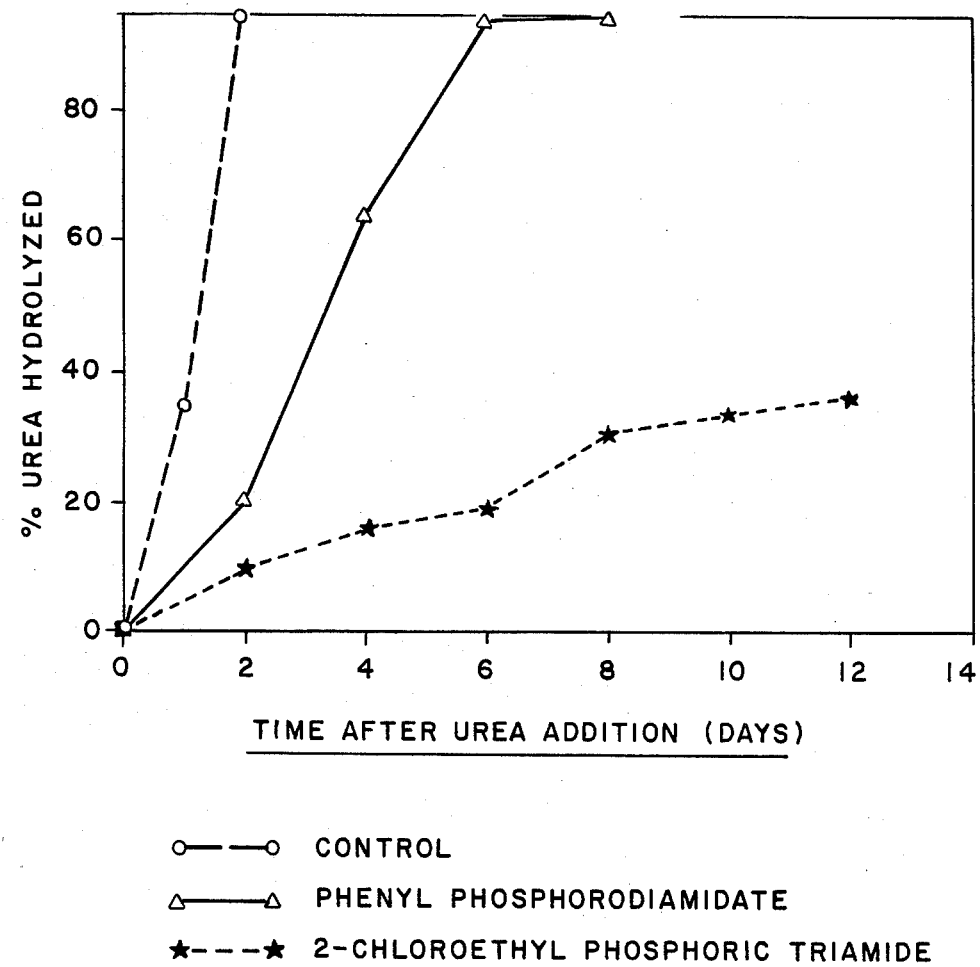

The application of a urease inhibiting effective amount of one or more of the above-identified phosphorotriamidate compounds to a plant growth media is essential for the practice of this invention. Preferably, the amount of the phosphorotriamidate compound employed is sufficient to inhibit the urease catalyzed hydrolysis of all urea which may be present in the plant growth medium. Usually these goals can be achieved if the composition contains at least about 0.01 parts of said one or more phosphorotriamidate compounds per one million parts of said plant growth medium. Hereinafter, the abbreviation "p.p.m." when employed is meant to designate parts by weight of said one or more phosphorotriamidate compounds per one million parts by weight of said plant growth medium. In the preferred embodiments of this invention, the amount of said one or more phosphorotriamidate compounds distributed in said plant growth medium is from about 0.01 to about 5000 ppm, and in the particularly preferred embodiments of the invention is from about 0.1 to about 1000 ppm. Amongst these particularly preferred embodiments of the invention, most preferred are those embodiments in which the amount of said one or more phosphoroamidate compounds distributed in said plant growth medium is from about 1 to about 500 ppm.

Within the limitations as set forth above, the preferred amounts to be employed of phosphorotriamidate compounds employed in the practice of this invention are dependent upon the particular situation. Thus, in determining the amount to be employed, consideration is made not only of the treatment need, i.e., soil pH, temperature, soil type, etc., but also of the mode of application to soil. When the one or more phosphorotriamidate compounds is to be applied in a broadcast application, the amount in p.p.m. may frequently be less than in row or band application where, for a substantial depth and width within the vicinity of application, there can be a very high concentration of the one or more phosphorotriamidate compounds. When application is made near the root zone or growing plants or when application is made immediately prior to seeding or transplanting, the amounts supplied are frequently at a lower rate than when application is made at the end of the growing season to prepare the soil for the following season. By dispersing very large dosages of the compounds in a plant growth media, a prolonged inhibition of the action of urease can be obtained over a period of many months. The concentration of the one or more phosphorotriamidate compounds is eventually reduced to a minimum by decomposition in the soil.

In one method for carrying out the present invention, one or more phosphorotriamidate compounds is distributed throughout the growth media in a broadcast application such as by spraying, dusting, distributing in irrigation water, etc. In such application, the one or more phosphorotriamidate compounds are supplied in amounts sufficient to permeate the growing area of soil with a urease inhibiting effective amount of one or more phosphorotriamidate compounds. In field administration, the one or more phosphorotriamidate compounds can be distributed in the soil in the amount and through such cross-section of the plant growth medium as to provide for the presence therein of a urease inhibiting effective amount of the one or more phosphorotriamidate compounds. It is usually preferred that the one or more phosphorotriamidate compounds be distributed below the surface of the soil or plant growth medium.

In another method for carrying out the present invention, one or more phosphorotriamidate compounds are administered to the plant growth medium in a band or row application. In such application, administration is made with or without a suitable carrier in amounts sufficient to supply to soil or growth medium a urease inhibiting effective amount of the one or more phosphorotriamidate compounds. After administration with or without discing or dragging, subsequent irrigation or rainfall distributes the one or more phosphorotriamidate compounds throughout the growth medium.

In one embodiment of the present invention, the one or more phosphorotriamidate compounds is distributed throughout the plant growth media prior to seeding or transplanting the desired crop plant.

In another embodiment, the soil is the root zone of growing plants is treated with the one or more phosphorotriamidate compounds in an amount effective to inhibit the action of urease but sublethal to plant growth. Phosphorotriamidate compounds which have little or no phytotoxicity can be employed advantageously at dosages of from 250, to 1000, to 5000 p.p.m. Such compounds are preferred for use in this embodiment of the invention. By following such practice, no adverse effect is exerted by the one or more phosphorotriamidate compounds upon growth of seeds or plants. Oftentimes, it is desirable to treat the soil adjacent to plants, and this procedure may be carried out conveniently in side-dressing operations.

In an additional embodiment, the soil is treated with the one or more phosphorotriamidate compounds in conjunction with the application of urea or one or more urea precursor compounds which are capable of forming urea in situ under the use conditions of the composition. The treatment with the one or more phosphorotriamidate compounds can be carried out prior to, subsequent to or simultaneously with the application of such urea fertilizers. Such practice prevents the rapid loss of the urea added as fertilizer by the action of soil bacteria. The administration to the plant growth medium of one or more phosphorotriamidate compounds in a urea based fertilizer composition constitutes a preferred embodiment of the present invention. Urea is a well known, commercially available compound and will not be discussed herein in detail. Illustrative of compounds which are believed to form urea on addition to the soil and are water-soluble urea formaldehyde condensation products, as for example, methylolureas, methyleneureas and mixtures thereof. These products and a method for their preparation is described in detail in U.S. Pat. No. 3,462,256. Still other useful sources of urea are water-insoluble urea formaldehyde condensation products such as ureaform. Illustrative of useful water-insoluble urea formaldehyde condensation products are those whose preparation and use are described in detail in U.S. Pat. Nos. 3,677,746 and 4,033,745.

The amount of urea or urea precursor compound included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quality of urea or urea precursor compound will vary from about 3 to about 40 weight percent on the aforementioned basis.

The fertilizer composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrients and macronutrients which may be deficient in the plant growth medium. The composition may also include plant growth regulators, as for example auxins, cytokinins and the like, as well as pesticides such as insecticides, miticides, herbicides, nematocides and the like and other fertilizers as for example ammonium nitrate.

The fertilizer composition of this invention can be conveniently used in the practice of the method of this invention to increase yields in a wide variety of plants including legume crop plants and cereal crop plants. For example, the required amounts of the composition may be applied to the soil immediately surrounding the plant, i.e., a radius up to about 20 feet, at a rate of application sufficient to obtain the desired increase in plant yield. The rate of application will depend on a number of factors, such as environmental conditions, type of crop plant and the like. The composition is usually applied at a rate of from about 5 to about 600 lbs. of urea nutrient per acre in a total applied aqueous volume of from about 3 to about 1500 gallons per acre. In the preferred embodiments of the method of this invention, the composition is applied at a rate of from about 2 to about 100 pounds of urea per acre in a total applied aqueous volume of from about 6 to about 250 gallons per acre, and in the particularly preferred embodiments of the invention the composition is applied at a rate of from about 3 to about 30 pounds per acre in a total volume of from about 9 to about 25 gallons per acre. The composition can be used in the soil or applied to the foliage of the plant, upon the seeds, or the roots of plants without injuring either the foliage, seeds or roots at any time during the growing cycle. Because of the action of the novel urease inhibitors present in the composition, all or a portion of the urease present at the situs of application will be inhibited and greater amounts of urea nutrients will be made available to the plant for longer periods of time.

The present invention can be carried out by distributing the one or more phosphorotriamidate compounds in an unmodified form through the plant growth medium. The present method also embraces distributing one or more such compounds as a consituent in a liquid or a finely divided solid composition. In such practice, the one or more phosphorotriamidate compounds can be modified with one or more additaments or soil treating adjuvants including water, petroleum distillates or other liquid carriers, surface-active dispersing agents, inert finely divided solids and other fertilizers such as reduced nitrogen fertilizers. Preferred adjuvants are surface-active dispersing agents, inert finely divided solids, and especially, urea; these adjuvants cooperate with the one or more organo phosphorotriamidatate compounds so as to facilitate the practice of the present invention, and to obtain an improved result. Depending upon the concentration of the one or more phosphorotriamidate compounds augmented compositions can be distributed in the plant growth medium without further modification or can be considered as concentrates and subsequently diluted with additional inert carrier to produce the ultimate treating composition. The required amount of the phosphorotriamidate can be supplied to growth media in from about 1 to about 50 gallons of organic solvent carrier, in from about 5 to about 27,000 or more gallons of aqueous carrier or in from about 20 to about 2000 pounds of solids carrier per acre treated. When an organic solvent carrier is employed, it can be further dispersed in the above volume of aqueous liquid carrier.

The concentration of one or more phosphorotriamidate compounds in compositions to be employed for the treatment of the plant growth media is not critical and can vary considerably provided the required dosage of effective agent is supplied to the growth media. In general, good results are obtained with liquid and solid compositions containing at least about 0.00001 percent by weight of the one or more phosphorotriamidate compounds based on the total weight of the composition, and in the particularly preferred embodiments of the invention the weight percent of one or more phosphorotriamidate compounds is from about 98 weight percent on the aforementioned basis. Amongst these particularly preferred embodiments most preferred are those embodiments in which the weight percent of said compounds contained in the composition is from about 0.002 to about 80, and ideally from about 0.01 to about 20 weight percent. Liquid or dust compositions in which the one or more phosphorotriamidate compounds is present in higher concentration can be uitlized as such or can be employed as concentrate compositions to be diluted to prepare actual treating compositions.

Liquid compositions containing the desired amount of the one or more phosphorotriamidate acid compounds can be prepared by dispersing the latter in one or more liquid carriers such as water or an organic solvent with or without the aid of a suitable surface active dispersing agent or emulsifying agent. Suitable organic solvents include acetone, di-isobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkyl aryl sulfonates, polyoxy-alkylene derivatives or sorbitol ester, sugar esters, complex ether alcohols, mahogany soaps and the like. The surface active agents are generally employed in the amount of from 1 to 20 percent by weight of the one or more phosphorotriamidate compounds.

Solid compositions containing the active one or more phosphorotriamidate compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more phosphorotriamidate compounds or wet with a liquid one or more phosphorotriamidate compounds or a solution of dispersion of a solid or liquid one or more phosphorotriamidate compounds in a volatile organic solvent. Depending upon the proportions of ingredients, these compositions can be employed without further modification or be considered concentrates and subsequently further diluted with solid surface active dispersing agent, talc, chalk, gypsum or the like to obtain the desired treating composition. Furthermore, such concentrate compositions can be dispersed in water with or without added dispersing agent or agents to prepare aqueous soil treating compositions.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, diaper treatment, pharmaceutical applications, urease inhibition in mammalian urinary tracks and the like. It should be noted that the particular active compound employed in one application may not necessarily be useful in another application. Thus, in the selection of a particular active material for use in an application, such factors as toxicity of the material, the environment in which the material will be used, level of urease inhibition desired and the like must be considered in selecting such material.

The phosphorotriamidate compounds which are employed as urease inhibitors in the composition of this invention are those of the formula:

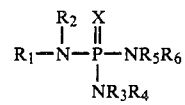

wherein:

X is sulfur or oxygen;

$R_1$ is alkyl substituted with one or more nucleophilic substituents;

$R_2$ is $R_1$, hydrogen, or substituted or unsubstituted alkenyl, alkynyl, cycloalkyl, cycloalkenyl, aralkyl or aryl, wherein permissible substituents are one or more trihalomethyl, alkyl, alkoxycarbonyl, halogen, nitro, phenoxy, isocyano, isocyanato, cyano, amino, alkylamino, dialkylamino, alkoxy, phenyl, mercapto, alkylmercapto, alkylcarbonyl, arylcarbonyl, carboxy or carboxamide groups in any combination; and $R_3$, $R_4$, $R_5$ and $R_6$ are the same or different and are individually hydrogen or alkyl having from 1 to about 4 carbon atoms.

Illustrative of permissible $R_1$ substituents are chloromethyl, 2,2-dichloroethyl, 2,2-dibromopropyl, 1-chloromethylethyl, 3,3-diiodobutyl, 2,2-dichloromethyl ethyl, 2,2,3,3-tetrachloropropyl, 2-phenoxyethyl, 2-cyanoethyl, 5-chloropentyl, 4-phenoxyhexyl, 2-iodo-2-phenylethyl, 2-acetylpropyl, 3-mercaptobutyl, 2-(p-toluenesulfonyl)ethyl, 2-benzenesulfonylpropyl, 2-(ethylsulfonyl)propyl, and the like.

Exemplary of useful $R_2$ substituents are the aforementioned $R_1$ substituents, hydrogen, methyl, ethyl, propyl, isopropyl, butyl, isobutyl, pentyl, neopentyl, hexyl, 2-butene, ethylene, 3-butene, 2-propene, acetylene, cyclopropyl, cyclobutyl, cyclopentyl, cyclohexyl, 2-nitroethyl, 5-halopentyl, 1-cyanoethyl, 2-dimethylaminopropyl, 3-methylaminobutyl, phenyl, 4-chlorophenyl, 3-pyridyl, 2-furyl, 2-naphthyl, benzyl, 3-nitrophenyl, 4-nitrophenyl, 4-halophenyl, 4-aminophenyl, 4-alkylphenyl, 4-alkoxyphenyl, 2-methylphenyl, 2,3-dimethylphenyl, 2,4-dimethylphenyl, 2,4,6-trimethylphenyl, 3-trifluoromethylphenyl, 4-cyanophenyl, 3-phenoxyphenyl, and the like.

Permissible $R_3$, $R_4$, $R_5$ and $R_6$ substituents include hydrogen, methyl, ethyl, propyl, and butyl.

The following compounds are illustrative of phosphorotriamidate compounds within the purview of the above structural formula which can be prepared simply by selecting appropriate reactants for use in the procedures described below and which can be employed in the practice of this invention.

2-bromoethyl phosphoric triamide 2-chloroethyl phosphorothioic triamide mercaptobutyl phosphoric triamide N-(2-morpholinoethyl)phosphoric triamide N-[2-(N-morpholinoethyl)phosphoric triamide ethyl 4-(diaminophosphinyl)aminobutyrate N-(2-phenoxyethyl)-N-methyl phosphoric triamide N,N-Bis-(2-fluoroethyl)phosphoric triamide 3-thiocyanopropyl phosphoric triamide N-(2-chloroethyl)-N-phenyl-N'-methyl phosphoric triamide N-(2-chloroethyl)phosphoric triamide
N,N-Bis-(2-chloroethyl)phosphoric triamide
N-(3-bromopropyl)phosphoric triamide
N-(2,2,2-trichloroethyl)phosphoric triamide
N-(2,2-dichloroethyl)phosphoric triamide
N-(2-cyanoethyl)phosphoric triamide
N-(2-chloroethyl)-N-methyl phosphoric triamide
N-(2-chloroethyl)-N'-methyl phosphoric triamide
N-(2-methylmercaptoethyl)phosphoric triamide
N-(3-methoxypropyl)phosphoric triamide
N-[2-(dimethylamino)ethyl]phosphoric triamide
N-(4-phenoxybutyl)phosphoric triamide
N-[2-(3,4-dihydroxyphenyl)ethyl]phosphoric-triamide
N-[2-(3,4-dimethoxyphenyl)ethyl]phosphoric-triamide
N-(2-phenylethyl)phosphoric triamide
N-(2-methoxybenyzl)phosphoric triamide
N-(2-chloroethyl(-N-ethyl phosphoric triamide
N-(3-bromopropyl)-N-(4-methoxyphenyl)-phosphoric triamide
N-(2-chloroethyl)-N-benzyl phosphoric triamide
N,N-Bis(3-bromopropyl)phosphoric triamide
N-(2-chlorocyclohexyl)phosphoric triamide
N-[2-(2-methoxyphenylethyl)]phosphoric triamide
N-[2-(4-methoxyphenylethyl)]phosphoric triamide
N-(2-phenoxyethyl)phosphoric triamide
N-(3-chlorododecyl)phosphoric triamide
N-(2-chlorohexyl)phosphoric triamide
N-(3-bromooctyl)phosphoric triamide
N-(2-idohexyl)phosphoric triamide
N-(perfluorobutyl)phosphoric triamide
N-(2-bromo-3-fluorohexyl phosphoric triamide
N-(2,3-dichlorobutyl)phosphoric triamide
N-(4-chlorobutyl)phosphoric triamide
N-(2,2,3,3-tetrachlorodecyl)phosphoric-triamide
N-(2,2-dichloro-3-bromooctyl)phosphoric-triamide
N-(2,2,2-trichlorovinyl)phosphoric triamide
N-(3-hexylmercaptopropyl)phosphoric triamide
N-(2-naphthyloxyisopropyl)phosphoric triamide
N-(2-mercaptoethyl)phosphoric triamide
N-(4-nitrophenyl)-N-3-chloropropyl phosphoric-triamide
N-[2-(N-methylamino)]-N-benzyl phosphoric-triamide
N-(2-hydroxyethyl)-N-(3-pyridyl)phosphoric-triamide
N-(2-ethoxyloxoethyl)-N-(2-naphthyl)phosphoric-triamide
N-(3-trifluoromethylphenyl)-N-(2,2-dichloroethyl)-phosphoric triamide
N-(4-methylmercaptophenyl ethyl)phosphoric-triamide
N,N-Bis-(4-methylmercaptophenylethyl)phosphoric triamide
N-(2,4-dimethylphenyl)-N-(3-cyanohexyl)phosphoric triamide
N-(2,4,6-trimethylphenyl)-N-(3-isocyanooctyl)phosphoric triamide
N-cyclohexyl-N-(2-chloroethyl)phosphoric-triamide
N-(2,2-difluoroethyl)phosphoric triamide
N-2-[N-piperidylpropyl)phosphoric triamide
N-(2-imidazoylylethyl)phosphoric triamide Preferred for use in the practice of this invention are phosphorotriamidate compounds in which:
X is oxygen;
$R_1$ is alkyl having from about 2 to 14 carbon atoms substituted with one or more chloro, fluoro, bromo, iodo, alkoxy, cyano, aryloxy, alkylamino, amino, dialkylamino, arylamino, alkylmercapto, mercapto, isocyano, isocyanato, acyloxy, hydroxy, alkoxycarbonyl, quaternary ammonium radicals, thiocyano, and arylmercapto groups at the alpha, beta, and/or gamma carbon atoms relative to the nitrogen moiety;
$R_2$ is $R_1$, 3-pyridyl, hydrogen, 2-furyl, 2-naphthyl, cinnamenyl, benzyl, phenyl or phenyl substituted by 3-nitro, 4-nitro, 2,3-dimethyl, 2,4-dimethyl, 2,4,6-trimethyl, 3-trifluoromethyl, 4-cyano, 4-phenyl, 4-methylmercapto, or 3-phenoxy; and
$R_3$, $R_4$, $R_5$ and $R_6$ are the same or different and are individually hydrogen or alkyl having from 1 to about 4 carbon atoms.

Particularly preferred for use in this invention are phosphorotriamidate compounds in which:
X is oxygen;
$R_1$ is alkyl having from about 1 to about 12 carbon atoms having at least one substituent on the alpha, beta or gamma carbon atoms relative to the nitrogen atom to which the $R_1$ group is bonded wherein the permissible substituents are selected from the group consisting of iodo, chloro, bromo, fluoro, or phenoxy;
$R_2$ is hydrogen; and
$R_3$, $R_4$, $R_5$ and $R_6$ are hydrogen.

Amongst these particularly preferred embodiments, most preferred for use in the practice of this invention are phosphorotriamide compounds in which:
X is oxygen;
$R_1$ is alkyl having from 1 to about 4 carbon atoms having one or more halo substituents on the alpha, beta and/or gamma carbon atoms relative to the nitrogen atom to which the $R_1$ group is bonded; and
$R_2$, $R_3$, $R_4$, $R_5$ and $R_6$ are hydrogen.

Especially efficacious compounds for use in the practice of this invention are N-(2-chloroethyl)phosphoric triamide and N-(3-bromopropyl)phosphoric triamide.

Compounds which are useful in the practice of this invention can be prepared in accordance with the following reaction scheme:

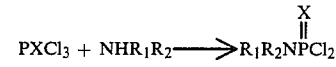

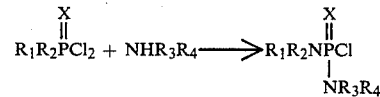

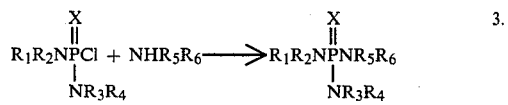

The aforementioned reaction is described in more detail in East German Pat. No. 128,315, Roth, H. J., et al., SYNTHESIS OF PHENYL PHOSPHORODIAMIDATES. PART I., Arch. Pharm., vol. 314, pp. 85–91, 1980, and references cited therein and will not be described herein in great detail.

Briefly stated, in each step of the three step reaction sequence, substantially equal molar amounts or excesses of the reactants are contacted neat or in an inert solvent, with or without a hydrogen chloride acid acceptor. The order in which the reactants are reacted indicated in the reaction scheme is for illustrative purposes only, and the order of reaction is not critical. Useful solvents include ethyl ether, methylene chloride, benzene, dioxane, toluene, carbon tetrachloride, xylene, tetrahydrofuran, methyl sulfoxide, dimethylformamide, and the like.

The acid acceptor employed is a basic material which can be either an inorganic or organic base. Suitable inorganic bases include alkali metal carbonates such as, sodium carbonate, potassium carbonate and the like. Organic bases which are used and preferred for use in the practice of this invention are tertiary amines, as for example, pyridine, 1,4-diazabicyclo[2.2.2]octane, isoquinoline, lutidine trimethylamine, triethylamine, and the like. In general, the molar ratio of acid acceptor to either reactant is substantially equimolar or a slight excess of the acid acceptor is employed.

Reaction temperatures and pressures are not critical. The reaction can be conveniently carried out at a temperature of from about $-20°$ C. to about 200° C., but is preferably carried out at a temperature of from about 25° C. to about 125° C. The reaction can be carried out at sub-atmospheric, atmospheric or super-atmospheric pressure. For convenience, the reaction is carried out at atmospheric or autogeneous pressure.

The exact proportions of the reactants are not crucial, some of the desired product being obtained when the reactants are employed in any proportions. However, in going to completion, the reaction consumes the reactants and the hydrogen chloride acceptor in equimolar proportions and the use of the reactants and the hydrogen chloride acceptor in such proportions is preferred.

Reaction temperatures are not critical and can be varied widely. The mixture is held within the desired reaction temperature range usually for a period of time, conveniently from about 2 to 8 hours before cooling. Good yields are obtained with reaction times of about 4 to 5 hours.

During the reaction, the hydrochloride salt of the hydrogen chloride acceptor forms and may precipitate from the mixture. This salt can be removed by such conventional procedures as extraction, filtration or centrifugation. The phosphorotriamidate compound can be separated by such conventional procedures as evaporation and purified by conventional procedures, such as distillation and extraction. The product separated as described above may be employed in the control of urease in soil or may be further purified by conventional procedures, such as extraction and distillation.

The following specific examples are present to more particularly illustrate the invention.

EXAMPLE I

Preparation of N-2-Chloroethyl Phosphoramidic Dichloride

A slurry is formed containing 8.5 g (0.073 mol) of 2-chloroethylamine hydrochloride and 26.7 g (0.174 mol) of phosphorus oxychloride. The slurry is heated for 3 hours at 100°–115° C. During the heating step hydrogen chloride gas evolved, and after the heating period the reaction mixture became a homogeneous solution. The reaction mixture was distilled to provide 10.0 g of 2-chloroethyl phosphoroamidic dichloride, boiling point 116°–118° C. at 0.15 mm.

NMR (CDCl$_3$): $\delta$5.5 (bs, 1H), 3.2–3.8 (m,4H).

EXAMPLE II

Preparation of N-2-Chloroethyl Phosphoric Triamide

A solution of 9.3 g of 2-chloroethylphosphoramidic dichloride in 25 ml of CH$_2$Cl$_2$ was added over a 30 minute time period to a solution of 10 g of ammonia in 125 ml of CH$_2$Cl$_2$. During the addition the mixture was held at a temperature of from $-15°$ C. to $-20°$ C. The reaction mixture was allowed to warm slowly to 20° C. over a 1.5 hr. time period, after which the solid product and byproduct NH$_4$Cl was collected by filtration. The crude reaction product was then subjected to Soxhlet extraction with CH$_2$Cl$_2$ to provide a pure product having a mp of 99°–101° C. after drying over P$_2$O$_5$.

NMR (DMSO-d6): $\delta$2.8–4.0 (complex multiplet);

IR (Nujol): 1560, 1310, 1245, 1200, 1155, 1130 and 930 cm$^{-1}$; and

Anal. Calcd for C$_2$H$_9$ClN$_3$OP: C, 15.25; H, 5.76; N, 26.67%÷Found: C, 15.50; H, 5.96; N, 26.36%.

EXAMPLE III

Preparation of N,N-Bis-(2-Chloroethyl)Phosphoric Triamide

The compound of Example II was prepared by a modification of the procedure of O. M. Friedman and A. M. Seligman, J. Am. Chem. Soc., 1954, 76 p. 655. The crude reaction product was purified by extraction with CH$_2$Cl$_2$ rather than recrystallization from acetone to give a material of mp 119°–120° C. (which depends on the heating rate).

Anal. Calcd. for C$_4$H$_{12}$Cl$_2$NO$_3$P: C, 21.83; H, 5.50; N, 19.10; Found: C, 21.68; H, 5.64; N, 18.89.

EXAMPLE IV

Preparation of N-(3-Bromopropyl)Phosphoramidic Dichloride

To a three-necked flask fitted with a thermometer, distillation column and a nitrogen tube was added 3-bromopropylamine hydrobromide (12 g, 0.055 mol) and 20 mL of POCl$_3$ (0.22 mol). The reaction mixture was heated to reflux under nitrogen overnight. Excess POCl$_3$ was removed at the pump at room temperature (attempted distillation resulted in decomposition). The crude dichloridate, 15.4 g, was used directly in the procedure of the following Example V.

NMR(CDCl$_3$): $\delta$5.55 (bs, 1H), 3.1–3.8 (m, 4H), 2.0–2.35 (m, 2H).

EXAMPLE V

Preparation of N-(3-Bromopropyl)Phosphoric Triamide

The crude 3-bromopropylphosphoramidic dichloride was added to a solution of 10 g of ammonia in 125 mL CH$_2$Cl$_2$ at $-30°$ C. The resulting mixture of product and NH$_4$Cl weighed 19.4 g. Extraction with CH$_2$Cl$_2$ gave a material which slowly discolored over several days, mp. 60°–65° C.

NMR (DMSO-d$_6$/D$_2$O): $\delta$3.45–3.9 (m, 7H, with singlet for NH complicating assignment of triplet for BrCH$_2$), 2.87 (dt, 2H, $\delta$CH$_2$CH$_2$N=7 Hz, $\delta$CH$_2$NHP=11 Hz), 1.9 (m, 2H).

EXAMPLE VI

Certain compounds were evaluated to determine their effectiveness as urease inhibitors. The inhibition tests were run in a New York State soil (Cazenovia sandy loam, pH 7.2). Evaluations (run in triplicate) consisted of applying 800 micrograms of test compound in 5 mL of water and 42.8 mg urea in 1 mL of water to 20 g of air-dry soil in a glass bottle. The bottle was capped with perforated aluminum foil and incubated at 25° C. for 3 days prior to extraction with 100 mL of 2M KCl solution containing 0.5 mg of phenylmercuric acetate. The extracts were then analyzed for remaining urea using an autoanalyzer. Percent inhibition was calculated as $$\% \text{ Inhibition} = \left(1 - \frac{A - B}{A - C}\right) \times 100\%$$

where A is urea recovered from unincubated sample (urea added to soil and immediately extracted); B is urea recovered from inhibited sample; and C is urea recovered from the control (uninhibited sample).

The results of these tests are set forth in the following Table I.

TABLE 1
PHOSPHORIC TRIAMIDES, $R_1R_2NPO(NH_2)_2$ INHIBITORS OF SOIL UREASE

| Experiment | $R_1$ | $R_2$ | % Inhibition 40 microgram per gram soil | % Inhibition 1 microgram per gram soil |
|---|---|---|---|---|
| 1 | $ClCH_2CH_2-$ | $-H$ | 100 | 77 |
| 2 | $ClCH_2CH_2-$ | $ClCH_2CH_2-$ | 30 | — |
| 3 | $BrCH_2CH_2CH_2-$ | H | 99 | 83 |

EXAMPLE VII

A series of tests were conducted to show the superior performance of the phosphorotriamidates used in the present invention over certain urease inhibitors known in the prior art. Employing the procedure of Example VI, the urease inhibiting activity at 35° C. of the prior art urease inhibitor, phenyl phosphorodiamidate, and N-(2-chloroethyl)phosphoric triamide were evaluated. In the evaluation, soil samples were taken every two days and analyzed for urea content. The results of this evaluation are set forth in FIG. 1.

FIG. 1 shows that N-(2-chloroethyl)phosphoric triamide is an excellent inhibitor even when soil temperatures are 35° C. (95° F.) for a period of 12 days. By comparison, phenyl phosphorodiamidate, a well known compound which has an excellent inhibitory effect on urease at 25° C., is much less effective at high soil temperatures, allowing essentially complete urea hydrolysis after only six days.

What is claimed is:

1. A composition comprising an acceptable carrier and a urease inhibiting effective amount of one or more phosphorotriamidate compounds of the formula:

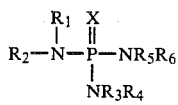

wherein:
X is oxygen or sulfur;
$R_1$ is alkyl substituted with one or more nucleophilic substituents;
$R_2$ is $R_1$, hydrogen, or substituted or unsubstituted cycloalkenyl, alkenyl, alkynyl, cycloalkyl, aralkyl, aryl or alkaryl wherein permissible substituents are one or more trihalomethyl, naphthoxy, alkyl, halogen, arylmercapto, phenoxy, phenyl, nitro, cyano, amino, alkylamino, dialkylamino, alkoxy, mercapto, alkylmercapto, alkylcarbonyl, arylamino, arylcarbonyl, alkoxycarbonyl, carboxy, diarylamino or carbonamide; and $R_3$, $R_4$, $R_5$ and $R_6$ are individually hydrogen or alkyl having from 1 to about 4 carbon atoms.

2. A composition according to claim 1 wherein said urease inhibiting amounts is at least about 0.00001 weight percent based on the total weight of the composition.

3. A composition according to claim 2 wherein said amount is from about 0.0001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 1 wherein X is oxygen.

7. A composition according to claim 1 wherein $R_1$ is substituted alkyl.

8. A composition according to claim 7 wherein $R_1$ is substituted alkyl having from 1 to about 8 carbon atoms.

9. A composition according to claim 8 wherein $R_1$ is substituted methyl, ethyl, propyl or butyl.

10. A composition according to claim 1 wherein $R_3$, $R_4$, $R_5$ and $R_6$ are individually hydrogen, methyl, or ethyl.

11. A composition according to claim 10 wherein $R_3$, $R_4$, $R_5$ and $R_6$ are individually hydrogen or methyl.

12. A composition according to claim 11 wherein $R_3$, $R_4$, $R_5$ and $R_6$ are hydrogen.

13. A composition according to claim 8 wherein $R_1$ is alkyl substituted with one or more substituents on the alpha, beta and/or gamma carbon atoms relative to the nitrogen atom to which $R_1$ is substituted.

14. A composition according to claim 13 wherein said $R_1$ is alkyl having one or more substituents substituted on the alpha and/or beta carbon atoms.

15. A composition according to claim 13 wherein said permissible substituents are selected from the group consisting of alkoxy, cyano, halo, amino, alkylmercapto, cyano, aryloxy, alkylamino, dialkylamino, mercapto, acyloxy, thiocyano, arylmercapto, arylamino, hydroxy, quaternary ammonium radicals, or alkoxycarbonyl.

16. A composition according to claim 15 wherein said permissible substituents are cyano, halo and phenoxy.

17. A composition according to claim 16 wherein said permissible substituents as halo.

18. A composition according to claim 17 wherein said permissible substituent is chloro, bromo or iodo.

19. A composition according to claim 14 wherein said one or more permissible substituent is substituted on the beta carbon atom.

20. A composition according to claim 17 wherein said permissible substituents as selected from the group consisting of 2-haloethyl, 2,2-dihaloethyl, 2,2,2-trihaloethyl, halomethyl, dihalomethyl, trihalomethyl, 2-halopropyl, 2,2-dihalopropyl, 2-halobutyl and 2,2-dihalobutyl.

21. A composition according to claim 17 wherein $R_1$ is alkyl having more than one halogen substituent substituted at the alpha, beta, and/or gamma positions relative to the nitrogen atom.

22. A composition according to claim 1 wherein $R_2$ is $R_1$ or hydrogen.

23. A composition according to claim 1 wherein $R_2$ is 3-pyridyl, 2-furyl, 2-naphthyl, cinnamenyl, benzyl, phenyl or phenyl substituted by 3-nitro, 4-nitro, 4-methylmercapto 2,3-dimethyl, 2,4-dimethyl, 2,4,6-trimethyl, 3-trifluoromethyl, 4-cyano, 4-phenyl or 3-phenoxy.

24. A composition according to claim 13 wherein $R_2$ is hydrogen.

25. A composition according to claim 17 wherein $R_2$ is hydrogen.

26. A composition according to claim 17 wherein $R_2$ is $R_1$.

27. A composition according to claim 20 wherein $R_2$ is hydrogen.

28. A composition according to claim 1 wherein said one or more compounds are selected from the group consisting of N-(2-chloroethyl)phosphoric triamide; N,N-bis-(2-chloroethyl)phosphoric triamide; and N-(3-bromopropyl)phosphoric triamide.

29. A composition according to claim 28 wherein said one or more compounds are selected from the group consisting of N-(2-chloroethyl)phosphoric triamide and N-(3-bromopropyl)phosphoric triamide.

30. An improved fertilizer composition comprising urea and/or one or more urea precursor compounds capable of forming urea when subjected to the use conditions of the composition, and a urease inhibiting effective amount of one or more of compounds of the formula:

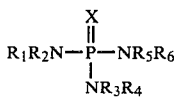

wherein:
X is oxygen or sulfur;
$R_1$ is alkyl substituted with one or more nucleophilic substituents;
$R_2$ is $R_1$, hydrogen or substituted or unsubstituted alkyl, cyloalkenyl, alkenyl, alkynyl, cycloalkyl, aralkyl, aryl or alkaryl wherein permissible substituents are one or more trihalomethyl, alkyl, halogen, phenoxy, phenyl, nitro, arylmercapto, cyano, amino, alkylamino, naphthoxy, dialkylamino, alkoxy, mercapto, alkylcarbonyl, arylcarbonyl, alkylmercapto, arylamino, diarylamino, alkoxycarbonyl, carboxy, or carbonamide; and
$R_3$, $R_4$, $R_5$ and $R_6$ are individually hydrogen or alkyl having from 1 to about 4 carbon atoms.

31. A method of enhancing plant growth and crop yield which comprises applying an effective amount of the composition according to claim 30 to soil immediately surrounding the plant.

32. A method of inhibiting the urease catalyzed hydrolysis of urea at a situs which comprises applying to said situs a urease inhibiting effective amount of one or more phosphorotriamidate compounds of the formula:

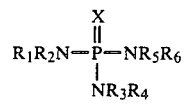

wherein:
X is oxygen or sulfur;
$R_1$ is alkyl substituted with one or more nucleophilic, substituents;
$R_2$ is $R_1$, hydrogen or substituted or unsubstituted alkyl, cycloalkenyl, alkenyl, alkynyl, cycloalkyl, aralkyl, aryl or alkaryl wherein permissible substituents are one or more trihalomethyl, alkyl, halogen, naphthoxy, phenoxy, phenyl, nitro, cyano, amino, alkylamino, arylmercapto, alkylmercapto, arylamino, diarylamino, dialkylamino, alkoxy, mercapto, alkylcarbonyl, arylcarbonyl, alkoxycarbonyl, carboxy, or carbonamide; and
$R_3$, $R_4$, $R_5$ and $R_6$ are individually hydrogen or alkyl having from 1 to 4 carbon atoms.

33. A method according to claim 32 wherein said situs is a plant growth medium.

34. A method according to claim 33 wherein said one or more compounds are applied to in said medium prior to application of urea to the said medium.

35. A method according to claim 32 wherein said urease inhibiting effective amount is at least about 0.01 ppm.

36. A method according to claim 35 wherein said amount is from about 0.01 to about 5000 ppm.

37. A method according to claim 36 wherein said amount is from about 0.1 to about 1000 ppm.

38. A method according to claim 37 wherein said amount is from about 1 to about 500 ppm.

39. A composition according to claim 1 wherein said carrier is a liquid.

40. A composition according to claim 39 wherein said liquid carrier is selected from the group consisting of water and organic liquids.

41. A composition according to claim 1 wherein said carrier is a finely divided inert solid.

42. A composition according to claim 1 wherein X is sulfur.

* * * * *